(12) United States Patent
Williams et al.

(10) Patent No.: US 6,699,210 B2
(45) Date of Patent: Mar. 2, 2004

(54) GLAUCOMA SHUNT AND A METHOD OF MAKING AND SURGICALLY IMPLANTING THE SAME

(75) Inventors: Stuart K. Williams, Tucson, AZ (US); Robert Snyder, Tucson, AZ (US)

(73) Assignee: The Arizona Board of Regents, Tucson, AZ (US)

( * ) Notice: Subject to any disclaimer, the term of this patent is extended or adjusted under 35 U.S.C. 154(b) by 43 days.

(21) Appl. No.: 09/300,388

(22) Filed: Apr. 27, 1999

(65) Prior Publication Data

US 2002/0156413 A1 Oct. 24, 2002

(51) Int. Cl.[7] .............................. A61F 9/00; A61F 11/00; A61M 31/00; B05D 3/00
(52) U.S. Cl. ......................... 604/8; 604/294; 604/521; 606/107; 623/905; 427/2.25
(58) Field of Search ............................ 604/8, 294, 97, 604/9, 10, 514, 521; 600/398, 399, 403, 404, 405, 406, 400–402; 606/107, 108, 151, 153–54, 159, 166; 128/898–99; 623/4.1, 11, 126, 6.1, 905–907; 427/2.1, 2.24–2.25, 2.28

(56) References Cited

U.S. PATENT DOCUMENTS

| | | |
|---|---|---|
| 4,428,746 A | 1/1984 | Mendez |
| 4,554,918 A * | 11/1985 | White |
| 4,633,863 A * | 1/1987 | Filips et al. ................ 128/165 |
| 4,875,468 A | 10/1989 | Krauter et al. |
| 4,968,296 A | 11/1990 | Ritch et al. |
| 5,041,081 A | 8/1991 | Odrich |
| 5,092,837 A | 3/1992 | Ritch et al. |
| 5,178,604 A | 1/1993 | Baerveldt et al. |
| 5,181,903 A | 1/1993 | Vann et al. |
| 5,300,020 A | 4/1994 | L'Esperance, Jr. |
| 5,338,291 A | 8/1994 | Speckman et al. |
| 5,370,607 A | 12/1994 | Memmen |
| 5,466,259 A | 11/1995 | Durette |
| 5,476,445 A | 12/1995 | Baerveldt et al. |
| 5,556,427 A | 9/1996 | Durette |
| RE35,390 E * | 12/1996 | Smith |
| 5,601,094 A | 2/1997 | Reiss |
| 5,665,114 A | 9/1997 | Weadock et al. |
| 5,713,955 A | 2/1998 | Durette |
| 5,716,660 A | 2/1998 | Weadock et al. |
| 5,722,948 A | 3/1998 | Gross |
| 5,743,274 A | 4/1998 | Peyman |
| 5,800,512 A | 9/1998 | Lentz et al. |
| 5,807,302 A | 9/1998 | Wandel |
| 5,824,046 A | 10/1998 | Smith et al. |
| 5,824,072 A * | 10/1998 | Wong |
| 5,824,073 A | 10/1998 | Peyman |
| 5,882,327 A * | 3/1999 | Jacob |

OTHER PUBLICATIONS

Jean T. Jacob et al., "Biocompatibility Response to Modigifed Baerveldt Glaucoma Drains, "1998 John Wiley & Sons Inc., pp. 99–107.*

Stuart K. Williams et al., "Denuleation Promotes Neovascularization of ePTFE in vivo", J. Biomater. Sci. Polymer Edn, vol. 0, No. 0, pp. 1–11 (1998).*

Jean T. Jacob et al. "Biocompatibility Response to Modified Baerveldt Glaucoma Drains", 1998 John Wiley & Sons Inc., pp. 99–107.

(List continued on next page.)

*Primary Examiner*—Angela D. Sykes
*Assistant Examiner*—Patricia Bianco
(74) *Attorney, Agent, or Firm*—Oblon, Spivak, McClelland, Maier & Neustadt, P.C.

(57) ABSTRACT

A glaucoma shunt including first and second porous regions laminated together, and a third region having edge areas fused to edge areas of the second region so as to form a hollow reservoir therebetween. Also included is a catheter having a first end sandwiched between the second and third regions and a second end to be implanted into an anterior region of an eye. A method of making and surgically implanting such a glaucoma shunt is also included.

30 Claims, 6 Drawing Sheets

OTHER PUBLICATIONS

Stuart K. Williams et al., "The Effects of Porosity on Endothelialization of EPTFE Implanted in Subcutaneous and Adipose Tissue", Section of Surgical Research, Department of Surgery, University of Arizona, Tucson, Arizona 85724, pp. 1–30.

Miriam K. Feldman, "What You Should Know About Aqueous Shunting Devices", Clinical Update Glaucoma, Oct. 1998, pp. 23–24.

Stuart K. Williams et al., "A Tissue Engineered Aqueous Drainage Device Constructed of EPTFE", Department of Surgery, Section of Surgical Research, Department of Ophthalmology, Arizona Health Sciences Center, Tucson Arizona, 85724 pp. 1–21.

James W. Karesh, M.D., "Polytetrafluoroethylene as a Graft Material in Ophthalmic Plastic and Reconstructive Surgery", Ophthalmic Plastic and Reconstructive Surgery 3(3): 179–185, 1987.

Hyun Bong Bae, M.D. et al, "A Membranous Drainage Implant in Glaucoma Filtering Surgery: Animal Trial", Kor. J. Ophthalmol. vol. 2: 49–56, 1988.

J.W. Karesh, M.D. et al., "Interpositional Polytetrafluoroethylene Grafts–Conjunctival Biocompatibility" Ophthalmic Plastic Reconstructive Surgery 7((4): 278–283, 1991.

Dong Myung Kim, M.D. et al., "Fibrous Capsule Surrounding Silicone Encircling Band and Gore–Tex™ Surgical Membrane", Korean J. Ophthalmol. vol. 5:51–58, 1991.

Jean–Marc Legeais et al., "Influence of ePTFE Polymer Implant Permeability on the Rate and Density of Corneal Extracellular Matrix Synthesis", Journal of Biomedical Materials Research, vol. 36, 49–54 (1997).

M.A. Fabrega et al., "Biocompatability of Polytetrafluoroethylene Grafts in Vitro and in Vivo Studies", Anatomy & Pathology Poster Presentation, p. 212 (abstract only).

John C. Galanis et al., "Use of Gore–Tex to Prevent Tissue Adhesion in a Rabbit Model of Glaucoma Filtration Surgery", Glaucoma Poster Presentation, p. 746 (abstract only).

Stuart K. Williams et al., "Denucleation Promotes Neovascularization of ePTFE in vivo", J. Biomater. Sci. Polymer Edn, vol. 0. No. 0. pp. 1–11 (1998) VSP 1998.

Jean T. Jacob–LaBarre et al., "Synthetic Scleral Reinforcement Materials: I. Development and in vivo Tissue Biocompatibility Response", Journal of Biomedical Materials Research, vol. 28, 699–712 (1994).

V. Jallet, et al., John Wiley & Sons, Inc., pp. 260–269, "Novel Synthetic Meshwork for Glaucoma Treatment. I. Design and Preliminary In Vitro and In Vivo Evaluation of Various Expanded Poly(Tetrafluoroethylene) Materials", 1999.

V. Jallet, et al., John Wiley & Sons, Inc., pp. 260–269, "Novel Synthetic Meshwork for Glaucoma Treatment. I. Design and Preliminary in vitro and in vivo Evaluation of Various Expanded Poly(Tetrafluoroethylene) Materials", 1999.

* cited by examiner

GLAUCOMA SHUNT AND A METHOD OF MAKING AND SURGICALLY IMPLANTING THE SAME

BACKGROUND OF THE INVENTION

1. Field of the Invention

The present invention is directed to implants, and in particular to glaucoma implants including biocompatible porous regions, which form a hollow reservoir with a base region so that excess aqueous humor may flow from the anterior chamber of an eye into the hollow reservoir. The invention is also directed to making and surgically implanting such implants.

2. Discussion of the Background

Glaucoma is a disease whereby the intraocular pressure (IOP) is too high for the health and viability of an optic nerve of an eye. If untreated, the high intraocular pressure eventually damages the optic nerve, and may lead to blindness.

Glaucoma can be controlled in many patients by lowering the IOP. This may be accomplished by using topical medications, laser treatment or trabeculectomy to increase an outflow of aqueous humor from the anterior chamber of the eye. When these methods fail to control intraocular pressure, ophthalmic surgeons may use setons, or aqueous drainage devices (glaucoma shunts) to remove aqueous humor from the anterior chamber, and thus reduce high levels of intraocular pressure. Currently, these devices are used as a secondary intervention because of their relatively high complication and failure rates.

Conventional glaucoma shunts, such as those disclosed in U.S. Pat. Nos. 5,338,291 and 5,476,445, both of which are incorporated by reference, include a catheter (i.e., a drainage tube) attached to a base plate. A free end of the catheter is surgically implanted into the anterior chamber of the eye. The base plate is sutured to an outside of the globe beneath the conjunctiva. The glaucoma implant functions as a drain over the first three to six postoperative weeks as the silicone plate is enclosed by a fibrous capsule. The fibrous capsule allows a space to form into which fluid can drain and from which fluid can be absorbed by the surrounding tissues. Ideally, the size and thickness of the fibrous capsule (i.e., the filtering bleb) that surrounds the base plate is such that the amount of fluid that passes through the capsule is identical to the amount of fluid produced by the eye at an intraocular pressure of 8 to 14 mmHg. Thus, aqueous humor can be drained from the anterior region of the eye, through the drainage tube to the filtering bleb, where the fluid can be absorbed by the surrounding tissue.

Conventional glaucoma shunts, such as the Molteno, Shocket, and Baervaldt glaucoma shunts, are made of silicone or polypropylene, a material approved for human implant use, but which exhibits biocompatibility difficulties when the material is implanted on the sclera underneath the conjunctiva of the eye. Thus, long term performance of these shunts is inadequate.

The primary cause of failure is a foreign body tissue response to the silicone or polypropylene material, which results in encapsulation of the drainage reservoir formed by the base plate of the shunt. Thus, the absorption of the drained aqueous humor is prevented, and an increased back pressure of the anterior chamber occurs. That is, in conventional glaucoma shunts, the healing response includes chronic inflammation and fibrosis of the shunt, which results in a decreased outflow of the aqueous fluid of the conjunctival space caused by the development of the fibrous capsule around the shunt.

One of the major approaches to solving the above-noted problems involves surface modification of the base polymer. For example, U.S. Pat. No. 5,338,291, discloses a method of texturing the surface of the base plate to interrupt the formation of a dense fibrous capsule and to promote vascularization around the base plate. Although these approaches have increased the life-time of the glaucoma shunt, the long-term function of the conventional glaucoma shunt is still inadequate.

SUMMARY OF THE INVENTION

Accordingly, one object of the invention is to provide a novel glaucoma shunt and a method of making and surgically implanting the same, which results in an improved healing response from surrounding tissues.

Another object of the invention is to provide a novel glaucoma shunt, which results in a dramatic reduction in the formation of a dense, fibrous capsule around the shunt.

Still another object of the invention is to provide a novel glaucoma shunt, which includes porous regions, so that new blood vessel growth occurs into pores, channels, or interstices of the porous material.

Yet another object of the invention is to provide a novel glaucoma shunt which has a long-term life expectancy.

These and other objects may be accomplished by providing a novel glaucoma shunt, including a first porous region, a second porous region connected to the first porous region, and a third region having edge areas attached to edge areas of the second region so as to form a hollow reservoir therebetween. Also provided is a catheter having an end between the second and third regions. In addition, the first and second regions may include, for example, expanded polytetrafluoroethylene (ePTFE), polyurethane, and elastomeric silicone, which have pores with diameters within a range of 1 $\mu$m to 500 $\mu$m. The second region may include, for example, expanded polytetrafluoroethylene (ePTFE), polyurethane, and elastomeric silicone, which have pores with diameters less than or equal to 0.8 $\mu$m. In addition, the connected first and second regions may have a permeability defined as a water flow through rate of at least 1.0 microliter/min·cm$^2$ at a water entry pressure of 100 mmHg.

Also provided is a method making the above novel glaucoma shunt. The method includes connecting (e.g., laminating or bonding) first and second porous regions 11 and 12, and then attaching (e.g., fusing or sealing) edge areas of a third region 13 to edge areas of the second region 11 so as to form a hollow reservoir therebetween. In addition, a catheter 7 having a first end is sandwiched between the second region 12 and third region 13.

In addition, a method of treating glaucoma using the above-noted novel glaucoma shunt is provided. This method includes surgically inserting one end of the catheter into the anterior chamber of the eye, and surgically implanting the base plate having the connected first and second porous regions attached to the third region beneath the conjunctiva of the eye.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
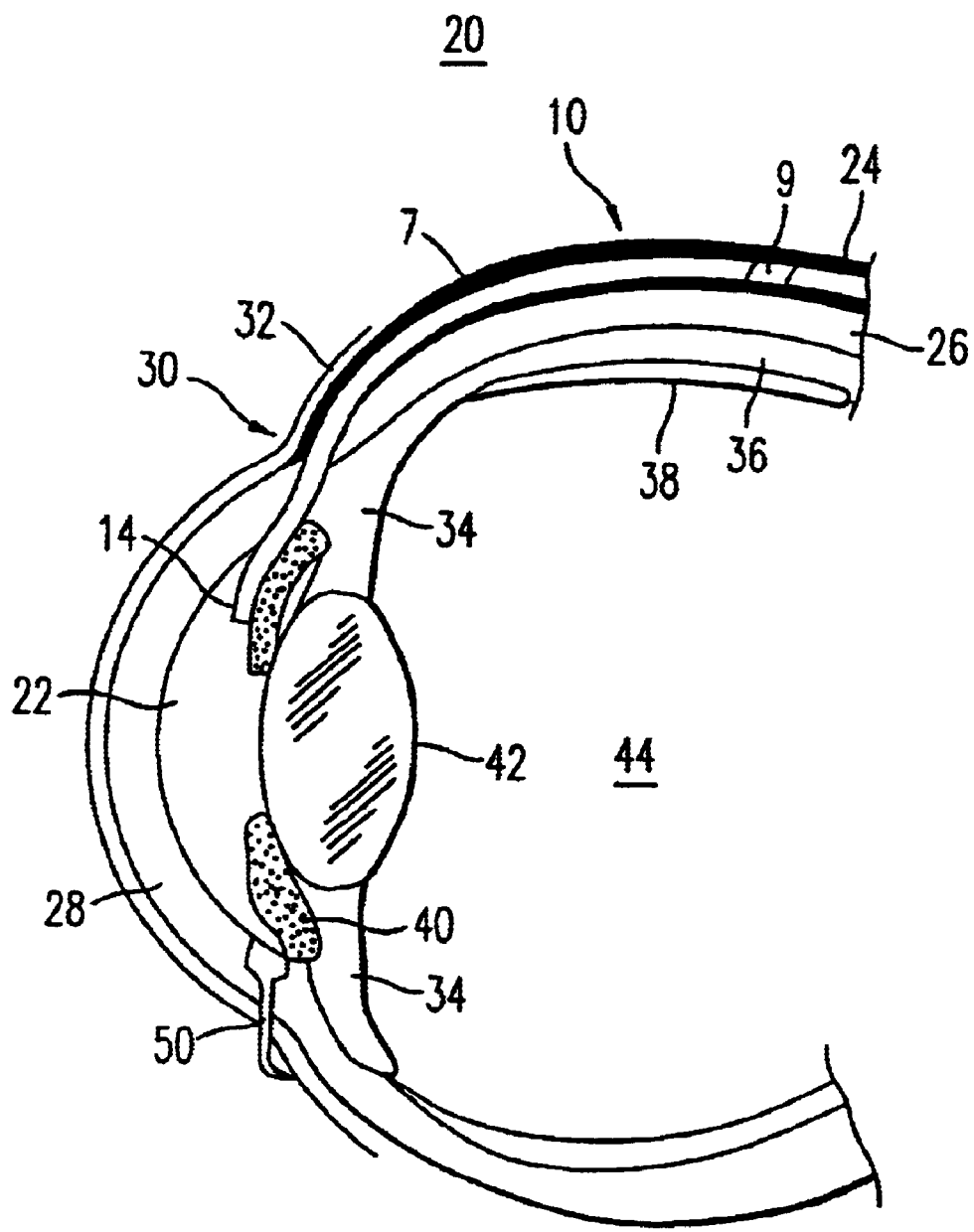
FIG. 1 is a fragmentary cross-section of an eye including an implanted glaucoma shunt of the present invention.

Referring now to the drawings, wherein like reference numerals designate identical or corresponding parts throughout the several views, to facilitate an understanding of the present invention, a brief description of an eye 20 will be first given with reference to FIG. 1. As shown, the eye 20 includes an anterior chamber 22 located between a cornea 28 and a lens 42. The cornea 28 merges into a sclera 26 at a junction called the limbus 30. A conjunctiva 32 extends from the limbus 30 over the front half of the eye to a position underlying the upper and lower eyelids. Also shown is a ciliary body 34 extending rearwardly until it becomes the chloride 36, which is adjacent to the retina 38. The chloride 36 is a region which contains many blood vessels. Further, an iris 40 controls the amount of light reaching the lens 42 positioned just behind the iris 40. A central portion of the eye 20 rearward of the lens 42 is called a vitreous cavity 44, whereas the portion forward of the iris 40 is called the anterior chamber 22. The anterior chamber 22 includes aqueous humor, which is a thin, watery eye fluid.

Aqueous humor is generated primarily by the ciliary body 34. In a normally functioning eye, this fluid is continuously drained to maintain a sufficient constant intra ocular pressure. The fluid drains through a tubicular mesh work (not shown), into the Schlemm canal 50, and out into the veins leaving the eye 20. Glaucoma results when this fluid does not properly drain.

Figure 2:
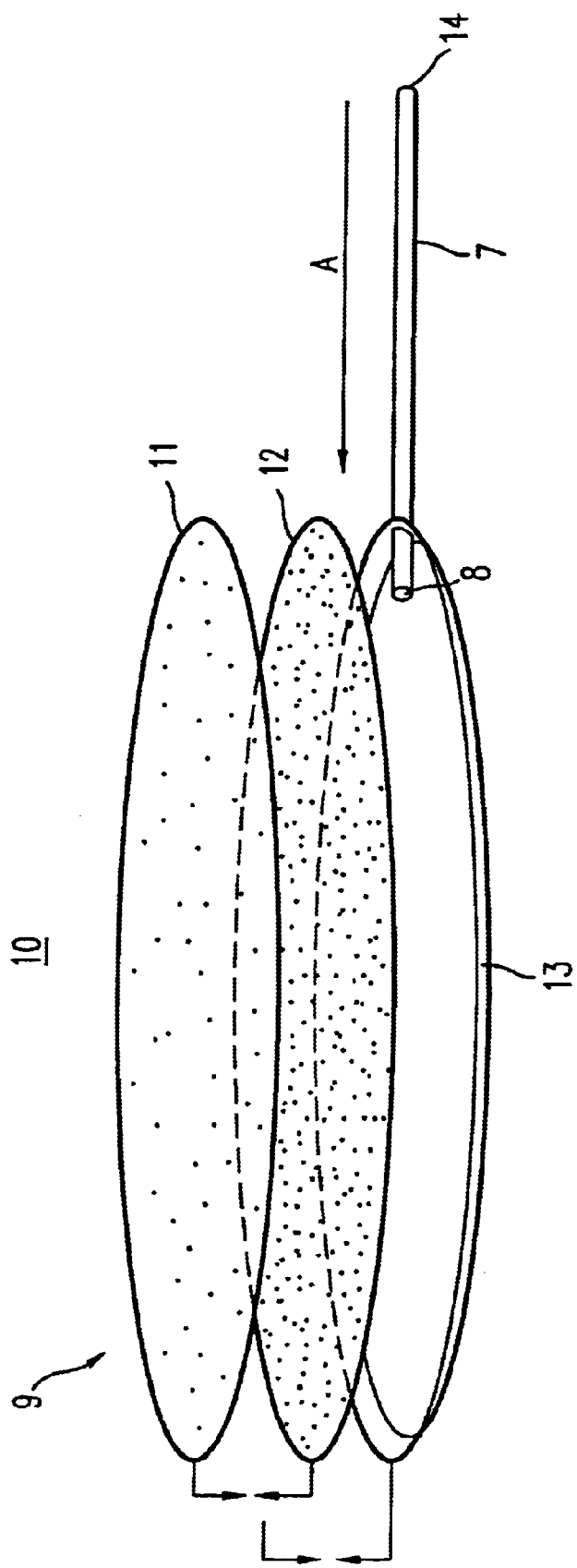
FIG. 2 is a perspective view of one example of a glaucoma shunt of the present invention.

One example of a glaucoma shunt 10 of the present invention is shown in FIG. 2 (note, the glaucoma shunt 10 is also shown implanted into the eye 20 in FIG. 1). As shown in FIG. 2, the glaucoma shunt 10 includes a base plate 9, and a catheter 7 (i.e., a drainage tube) having a first end 8 and a second end 14. The second end 14 is surgically implanted into the anterior chamber 22 of the eye 20. An attaching mechanism including suture holes (not shown) may also be provided on the base plate 9, so that a surgeon may suture the shunt 10 directly to the sclera 26.

The base plate 9 includes a first porous region 11, and a second porous region 12 connected to the first porous region 11. The regions may be connected by, for example, laminating or bonding the regions together. Other suitable connecting methods may also be used. It should be noted that more than two porous regions may be used, i.e., three, four, etc. regions. The base plate 9 also includes a third region 13 having edge areas which are attached (e.g., sealed or fused) to edge areas of the second region 12 so as to form a hollow reservoir therebetween. In addition, the first, second and third regions may be individual layers (i.e., first, second and third layers) or may include a single layer with a plurality of regions or zones of porosity.

Figure 7:
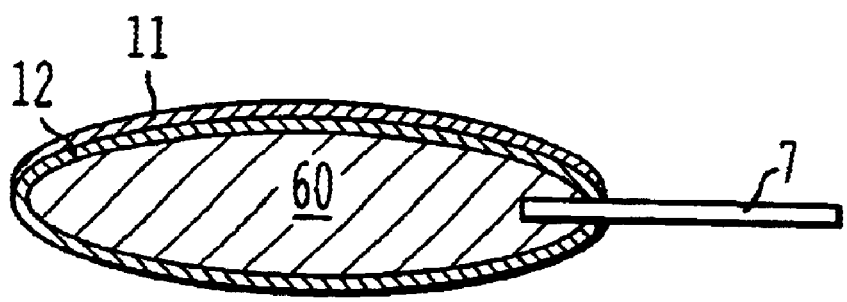
FIG. 7 is another perspective view of a glaucoma shunt of the present invention.

The catheter 7 may be connected to the base plate 9 by, for example, sandwiching the first end 8 between the second region 12 and third region 13. Thus, excess aqueous humor can flow from the anterior chamber 22 into the hollow reservoir 60 (see FIG. 7, for example) via the catheter (as indicated by the Arrow A), and then out to surrounding tissue via the first and second porous regions 11 and 12.

The material used to form the first and second regions 11 and 12 may be, for example, any one of expanded polytetrafluoroethylene (ePTFE), polyurethane, and elastomeric silicone. Any combination thereof may also be used. In addition, the first region 11 includes pores or channels with diameters sufficient to allow blood vessels to pass through, such as diameters within a range of 1 $\mu$m to 500 $\mu$m. The second region 12 includes pores or channels with a smaller diameter sufficient to not permit cellular entry, such as diameters less than or equal to 0.8 $\mu$m. The pores or channels may be formed using leachable salt inclusion at the time of polymer extrusion or by physically creating pores or channels using mechanical devices, such as drills, or by optical devices, such as lasers.

In addition, the pores or channels of ePTFE may also be referred to as "internodal distances," which is considered a measure of porosity. A more detailed description of internodal distances is described in the document "The Effects of Porosity on Endothelialization of ePTFE Implanted in Subcutaneous and Adipose Tissue" by Salzman et al, J Biomed. Mater. Res., which is herein incorporated by reference in its entirety.

In addition, the connected first and second regions 11 and 12 include a permeability defined as a water flow through rate of at least 1.0 microliter/min·cm$^2$ at a water entry pressure of 100 mmHg, which provides an assessment of relative porosity. The third region 13 may include polypropylene to form a supporting polypropylene disk. The catheter 7 may be formed with silicone, ePTFE, polycarbonate, polyethylene, polyurethane, or any combination thereof, and have an inner diameter sufficient to allow flow of aqueous humor from the anterior chamber 22 to the hollow reservoir, such as a diameter of about 0.3 mm, for example.

Thus, when the glaucoma shunt 10 is implanted into the eye 20 (see FIG. 1), aqueous humor may flow from the anterior chamber 22 into the second end 14 of the catheter 7 and then flow into the hollow reservoir formed in the base plate 9. In addition, because the first and second regions 11 and 12 are formed with a porous material, the aqueous humor may flow out of the hollow reservoir and be absorbed by surrounding tissue. Further, because the first region 11 includes a porous material having pores or channels sufficient in diameter to allow blood vessels to pass through, a stimulation of new blood vessels in this area can be achieved. In addition, because the second region 12 includes a porous material with pores or channels which prevent cellular entry, the new stimulated blood vessels are prevented from entering the hollow reservoir, thereby maintaining the integrity of the reservoir.

The size (length, width and thickness) of the shunt is that suitable for surgically implanting the shunt into the eye. For example, the catheter may comprise a length between 1 mm and 10 cm, and an inner diameter of about 0.05 mm to 2.0 mm, for example. In addition, a maximum length and width of the shunt may be 4 cm, a minimum length and width of the shunt may be 1 mm, and a thickness of the shunt may be between 1 mm and 1 cm. The length is defined as a distance from the outermost surface of the base plate 9 to the second end 14 of the catheter 7. The width is defined as the maximum width (diameter) of the base plate 9. The shape of the base plate 9 may be, for example, circular, spherical, elliptical and be curved to conform with a shape of the sclera 26. Other shapes and sizes suitable for implanting the glaucoma shunt into the eye may be used without departing from scope of the invention.

In addition, a biocompatibilty of the glaucoma shunt may be improved (i.e., modified) with chemicals so that the subsequent healing response of tissue in association with the material forming the regions is altered once the glaucoma shunt is implanted. The alteration in healing response is defined as a reduction in inflammatory response typically seen with polymeric materials, and includes a reduced presence of macrophages and foreign body giant cells. The chemical modifications may include the covalent interaction of the chemical species with polymer, by using, for example, a process provided by SurModics Inc. under the trademark PHOTOLINK™. In addition, the chemical modifications include the absorption of the applied chemical species into the polymers. These chemical modifications include the use of proteins and peptides with known affects on cellular function, such as the reduction in inflammation, reduction in fibrous capsule formation by inhibiting the proliferation of cells found in developing fibrous capsules, inhibition of extracellular matrix protein synthesis by cells in the fibrous capsule, and/or stimulation of angiogenesis from existing vessels in the tissue surrounding the catheter and base plate of the implanted glaucoma shunt. The chemical treatment may include any one, or a combination of, extracellular matrix proteins selected from the group consisting of collagen type I, collagen type III, collagen type IV, osteopontin, laminin type 1, laminin type 5, laminin type 10/11, fibronenctin, and peptide sequence RGD.

Further, a "denucleated" material reduces the inflammatory response of tissue surrounding the implant, and increases neovascularization (i.e., increase in new blood vessels) in tissue surrounding the material. That is, the glaucoma shunt (e.g., the base plate as well as the catheter) may comprise a material selected from the group consisting of denucleated polytetrafluoroethylene (ePTFE), denucleated polyurethane, and denucleated elastomeric silicone, such that at least 60% of air trapped within the material is removed. Denucleation is a process which removes air trapped within the material.

The modification of surface properties of implantable polymers and the process of denucleation is described in more detail in the document "Denucleation promotes neovascularization of ePTFE in vivo," by Boswell et al, J. Biomater. Sci. Polymer Edn, Vol 0, No. 0, pp. 1–11 (1998), which is herein incorporated by reference in its entirety. Further, the process of denucleation is also described by Klitzman et al, J. Biomed. Mater. Res. 29, 1039 (1995), which is herein incorporated by reference in its entirety.

FIGS. 3–5 and 6A–6B illustrate one example comparing a denucleated ePTFE glaucoma shunt with a conventional Baerveldt shunt.

EXAMPLE 1

Figure 3:
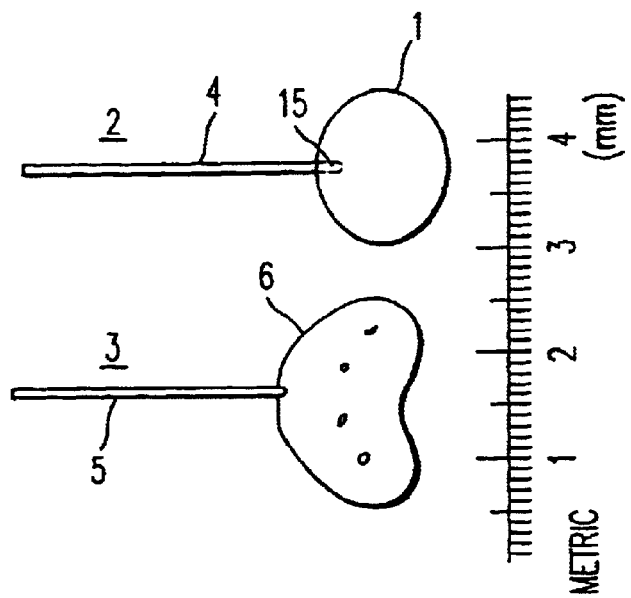
FIG. 3 is a perspective view illustrating glaucoma shunts used in one example of the present invention.

This example compares a denucleated ePTFE shunt with a conventional Baerveldt shunt, both of which were implanted into the eyes of rabbits. In more detail, FIG. 3 illustrates a denucleated ePTFE shunt 2 and a conventional child's size Baerveldt shunt 3. Note that the catheter 5 (i.e., silicone tube) drains onto a top surface of the Baerveldt shunt 3, whereas the catheter 4 drains to the underside of the denucleated ePTFE shunt 2. The glaucoma shunt 2 includes a disk 1 (i.e., a base plate) of denucleated ePTFE, approximately 15 mm in diameter, with a 60 $\mu$m internodal distance. A second end 15 of the catheter 4, which includes a 0.63 mm inside diameter, was forced through a 23 ga hole made near a center of the disk 1 and held in place by compression. Three child's size Baerveldt shunts 3 and five denucleated ePTFE shunts 2 were implanted into the eyes of New Zealand rabbits (female, white, 3 kg).

Prior to implantation, the ePTFE base plates 1 were sterilized by steam autoclave, then denucleated by a series of ethanol soaks, 10–20 minutes each, starting at 100% and decreasing by 10% steps to 0% ethanol in diH$_2$O. Complete denucleation was noted by the transition from white (dry) to a uniform, nearly transparent appearance of the ePTFE disks 1. The ePTFE disks 1 were then soaked in two washes of phosphate buffered saline (PBS; 2.7 mM KCl, 1.5 mM KH$_2$PO$_4$, 137 mM NaCl, 8.1 mM Na$_2$HPO$_4$, pH 7.4), and stored at room temperature overnight. The Baerveldt shunts 3 were implanted immediately after removal from their sterile packaging with no additional processing.

NIH guidelines for the care and use of laboratory animals (NIH Publication #85–23 Rev. 1985) were observed throughout this example. The rabbits were anesthetized with 35 mg/kg ketamine IM. The conjunctiva was opened at the limbus and the shunts were placed onto the sclera and sutured in two places. A 23 ga opening was created in the anterior chamber at the limbus and the catheters were inserted. The conjunctive was closed with a vicryl suture and the eye was treated with a topical steroid/antibiotic for 1 wk postoperatively. Intra ocular pressure measurements were made with a pnuemotonometer periodically over the course of this example.

After eight weeks, the rabbits were euthanized and their eyes were removed and fixed for histological examination. Six micron-thick paraffin sections were stained with hematoxylin and eosin for evaluation of overall tissue organization. Additional serial sections were stained with trichrome to evaluate collagen composition of the healing tissue or with an anti-factor VIII antibody to identify neovascularization near the implants. For the vascular staining, sections were rehydrated, then blocked with 5% non-fat dry milk for 30 min. The sections were then incubated with an anti-factor VIII antibody (at 1:100) for 1 hr, washed, and then incubated with a rabbit anti-goat secondary antibody conjugated to horseradish peroxidase. After one hour, the sections were washed, then incubated with diaminobenzidine until a dark brown precipitate developed at labeled endothelial cells. After further washing, the sections were then counterstained with methyl green. Two regions along the length of each implant were assessed for vascular profiles. That is, blood vessels were counted in a proximal region within 52 $\mu$m of the polymer/tissue interface, as well as a distal region between 53 and 104 $\mu$m of the polymer/tissue interface.

Results

In this example, the healing and functional characteristics of the Baerveldt shunts, one of the most widely used commercial devices, and the denucleated ePTFE shunts were compared. The results of this example are illustrated in FIGS. 4, 5 and 6A–6B.

Figure 4:
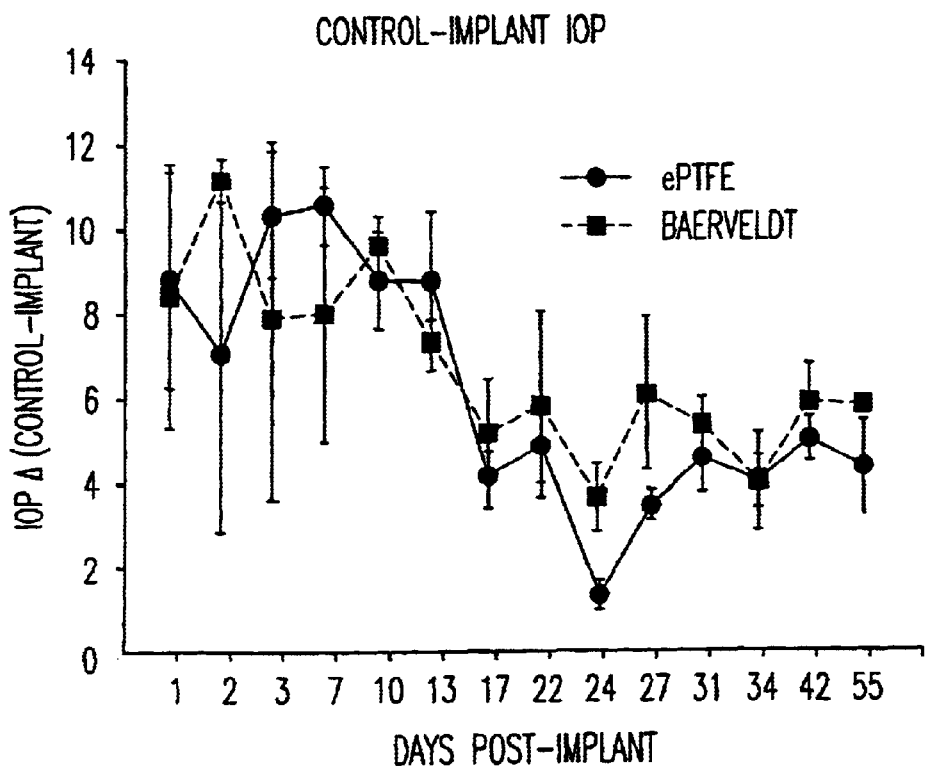
FIG. 4 is a graph illustrating a comparison of intra ocular pressure differential between a normal eye and an implanted eye including the glaucoma shunts illustrated in FIG. 3.
Figure 5A:
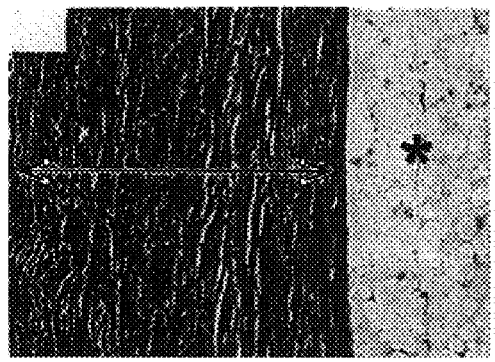
FIG. 5 illustrates photomicrographs of sections of explanted shunts illustrated in FIG. 3 after 55 days in vivo.
Figure 5B:
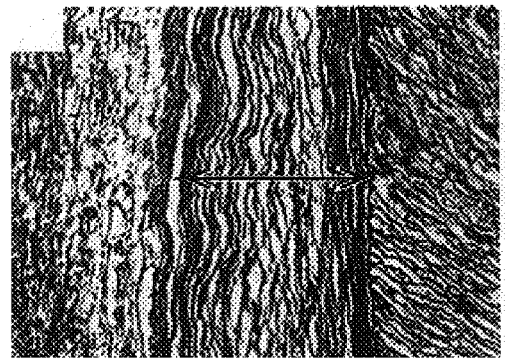
Figure 5C:
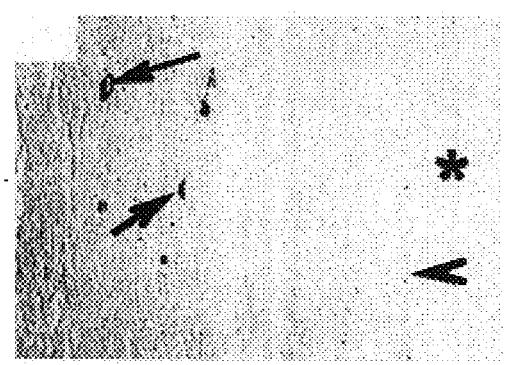
Figure 5D:
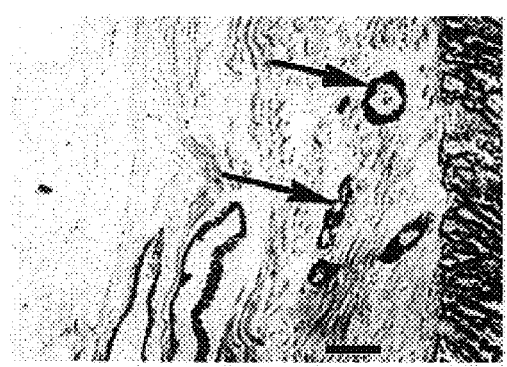

FIG. 4 is a graph illustrating intra ocular pressure measurements taken over the course of this example. The data shown is the mean ∓Standard Error of the Measurement (SEM) for the Baerveldt implants (shown as squares symbols) and the denucleated ePTFE implants (shown as round symbols). FIG. 4 shows a typical response to implantation of an aqueous drainage device. That is, initially the IOP was reduced by about 50% from control eyes (i.e., eyes without implants) for the first two weeks, then stabilized at approximately 30% of the contralateral control IOP. No significant differences in functional characteristics, as assessed by IOP measurements, were discerned between the conventional Baerveldt shunts and the denucleated ePTFE shunts.

The denucleated ePTFE device was designed to accept aqueous fluid between the surface of the eye and the polymer, rather than onto the surface of the device, and thus no bleb was formed. A space was seen under the ePTFE disk, presumably where fluid collected, but the overall thickness of the device with associated tissues was less than half of that observed with the commercial Baerveldt device (data not shown).

FIG. 5 illustrates photomicrographs of sections of the explanted shunts after 55 days in vivo. Reference letters "A" and "B" represent the section stained with hematoxylin and eosin. The double arrow in section A illustrates the capsule thickness on a distal surface of the Baerveldt shunt, and the double arrow in section B illustrates the capsule thickness on a distal surface of the denucleated ePTFE shunt. Reference letters "C" and "D" respectively represent immunohistochemical stained section using an anti-Factor VIII antibody of the Baerveldt and denucleated ePTFE shunt to identify vascular profiles in tissue adjacent to the shunts (the arrowhead identifies the edges of tissue). The asterisks indicate the location of the space occupied by the fluid bleb over the Baerveldt material. The bar symbol equals a distance of 50 $\mu$m.

As shown in FIG. 5, microscopic examination of the explanted tissues revealed a fibrous capsule of varying thickness along a length of each of the two shunt types. The tissue response was primarily fibrotic. That is, a capsule of dense irregular connective tissue with few to no inflammatory cells present. The Baerveldt shunt appeared to have a relatively thick, dense fibrous capsule forming a bleb which was readily distinguishable from the overlaying irregular connective tissue of the conjunctiva. The denucleated ePTFE shunt also had a distinct capsule, but it appeared thinner and less dense, was tightly associated with the polymer, and occasional blood vessels could be discerned near the polymer. Thus, histological examination indicated that the tissue on the distal side of the Baerveldt device was thicker, denser and less vascularized than the denucleated ePTFE shunt. Trichrome stain, in which collagen stains blue, suggested that collagen was the predominant extracellular matrix comprising the capsule around both devices (data not shown).

Figure 6A:
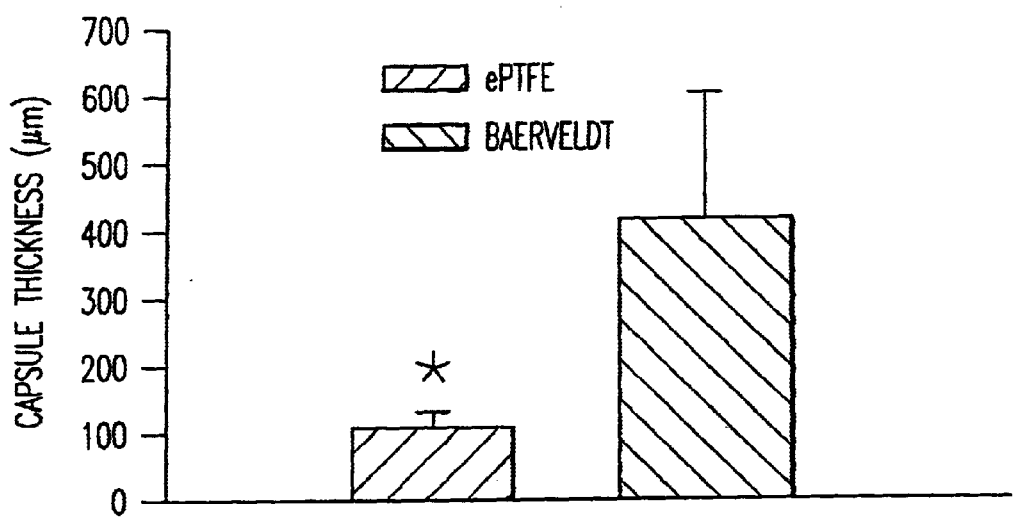
FIG. 6A is a histogram illustrating a capsule thickness ($\mu$m) associated with the glaucoma shunts illustrated in FIG. 3.
Figure 6B:
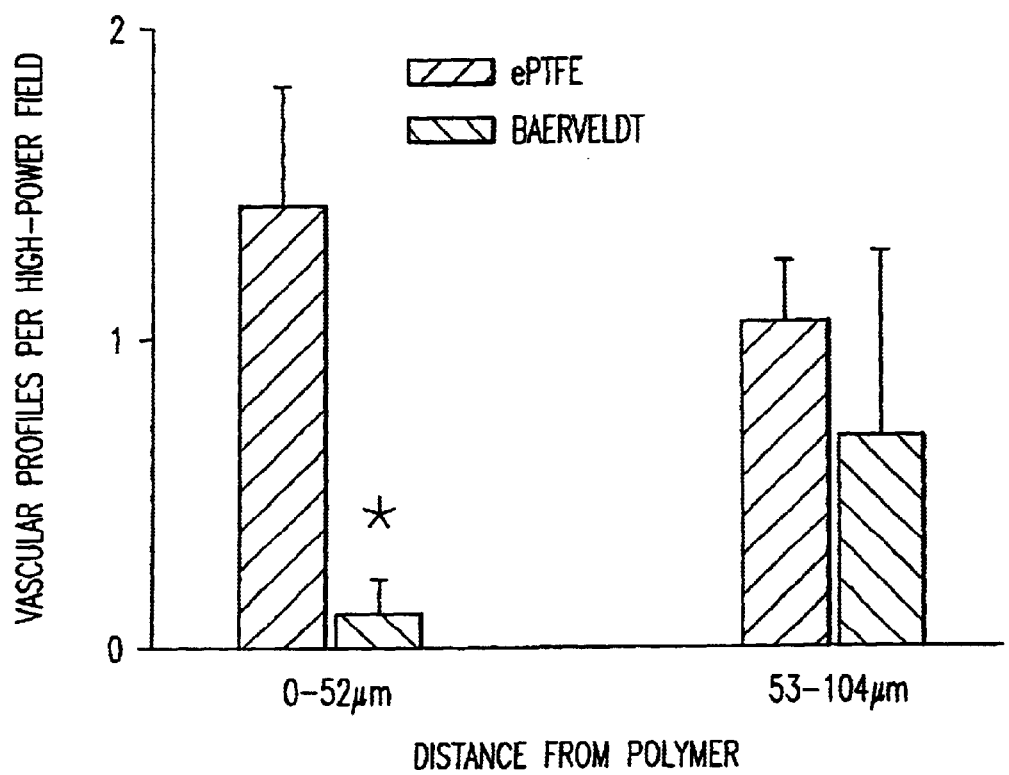
FIG. 6B is a histogram illustrating vascularity profiles associated with the glaucoma shunts illustrated in FIG. 3.

FIGS. 6A and 6B are histograms respectively illustrating a capsule thickness and vascularity associated with each implant. That is, FIG. 6A illustrates a comparison between a fibrous capsule thickness associated with each implant, and FIG. 6B illustrates a comparison between the vascular profile counts of tissue sections stained with the anti-Factor VIII antibody for each implant. One count was made parallel with the polymer from 0–52 $\mu$m into the surrounding tissue, and another count was made in the same fashion from 53–104 $\mu$m into the tissue. Asterisks indicate significant differences at $P<0.05$ using the unpaired students E-test.

As shown in FIG. 6A, measurements of the capsule thickness revealed a fibrous capsule associated with the denucleated ePTFE shunt that was approximately 75% thinner than the Baerveldt shunt. In addition, as shown in FIG. 6B, there were more than 10 times the number of vessel profiles within close proximity (52 $\mu$m) to the denucleated ePTFE as compared with the Baerveldt shunt.

These results indicate that the denucleated ePTFE can act as a functional aqueous drainage device material, providing a maintenance of IOP at levels comparable with the Baerveldt shunt. Further, the collected data confirms the denucleated ePTFE shunt develops a thinner, less dense capsule. Thus, the flow of aqueous fluid into the subconjunctival space would be less restricted. Accordingly, the denucleated ePTFE shunt with its thinner capsule can function longer than the Baerveldt shunt.

In addition, the close proximity of vessels to the denucleated ePTFE shunt, as compared with the Baerveldt shunt, illustrates the novel material and design improve the functionality of the shunt. The vessel caliber around the denucleated ePTFE shunt is suggestive of a microcirculation network, that portion of the circulation which can reabsorb interstitial fluids. Aqueous humor is a fluid with low colloid osmotic pressure, favoring diffusion into a site of higher colloid content such as blood. Thus, the presence of these vessels provides an additional source for reabsorption; in essence a surrogate to the episcleral vascular network.

A method of making the above novel glaucoma shunt will now be described with reference to FIG. 2. The first and second porous regions 11 and 12 are connected together (e.g., by laminating or bonding the regions), and then edge areas of a third region 13 are attached (e.g., fused or sealed) to edge areas of the second region 11 so as to form a hollow reservoir therebetween. In addition, an end of the catheter 7 is inserted between the second region 12 and third region 13.

The method may also include denucleating at least one of the first, second, and third regions 11, 12 and 13 so as to remove at least 60% of air trapped within a material comprising the at least one of the first, second and third regions. Further, the denucleating step may be performed using a graded series of alcohol baths followed by a series of washes with denucleated water to remove residual alcohol left by the alcohol baths. Alternatively, the denucleating step may be performed using hyperbaric conditions defined as a high pressure greater than 250 mmHg while the shunt is submerged in an aqueous solution, or performed in a vacuum defined as a pressure less than 50 torr. The shunt may also be treated with extracellular matrix proteins selected from the group consisting of collagen type I, collagen type III, collagen type IV, osteopontin, laminin type 1, laminin type 5, laminin type 10/11, fibronenctin, and peptide sequence RGD. The shunt may also be stored in a denucleated aqueous environment until it is ready for use.

Further, a method of treating glaucoma using the above-noted novel glaucoma shunt is provided. This method includes surgically inserting one end of the catheter into the anterior chamber of the eye, and surgically implanting the base plate having the connected first and second porous regions attached to the third region beneath the conjunctiva of the eye.

The glaucoma shunt according to the present invention has numerous advantages over the conventionally available glaucoma shunts. Some advantages are, for example, an improved healing response from surrounding tissues (e.g., improved biocompatibility), dramatic reduction in the formation of a dense, fibrous capsule around the shunt, and an increased life expectancy of the device. Further, in one example, the catheter is "sandwiched" between regions and thus an extra bonding step may be omitted.

Obviously, numerous modifications and variations of the present invention are possible in light of the above teachings. It is therefore to be understood that within the scope of the appended claims, the invention may be practiced otherwise than as specifically described herein.

What is claimed is:

1. A glaucoma shunt, comprising:
   a first porous region;
   a second porous region connected to the first porous region and having edge areas;
   a third region having edge areas attached to the edge areas of the second region so as to form a hollow reservoir therebetween; and
   a catheter having an end between the second and third regions,
   wherein the first, second and third porous regions and the catheter form the glaucoma shunt,
   wherein at least one of the first, second and third regions comprises a material selected from the group consisting of denucleated polytetrafluoroethylene (ePTFE), denucleated polyurethane, and denucleated elastomeric silicone, in which at least 60% of air trapped within the material is removed, and
   wherein the second region comprises denucleated expanded polytetrafluoroethylene (ePTFE) having pores with diameters less than or equal to 0.8 μm.

2. The shunt according to claim 1, wherein the first region comprises denucleated expanded polytetrafluoroethylene (ePTFE) having pores with diameters within a range of 1 μm to 500 μm.

3. The shunt according to claim 1, wherein the connected first and second regions have a permeability defined as a water flow through the rate of at least 1.0 microliter/min·cm$^2$ at a water entry pressure of 100 mmHg.

4. The shunt according to claim 1, wherein the first region comprises denucleated polyurethane having pores with diameters within a range of 1 μm to 500 μm.

5. The shunt according to claim 1, wherein the second region comprises polyurethane having pores with diameters less than or equal to 0.8 μm.

6. The shunt according to claim 1, wherein the first region comprises elastomeric silicone having pores with diameters within a range of 1 μm to 500 μm.

7. The shunt according to claim 1, wherein the second region comprises elastomeric silicone having pores with diameters less than or equal to 0.8 μm.

8. The shunt according to claim 1, wherein at least one of the first, second and third regions comprises extracellular matrix proteins selected from the group consisting of collagen type I, collagen type III, collagen type IV, osteopontin, laminin type 1, laminin type 5, laminin type 10/11, fibronenctin, and peptide sequence RGD.

9. The shunt according to claim 1, wherein the catheter comprises material selected from the group consisting of silicone, ePTFE, polycarbonate, polyethylene, and polyurethane, and has a length between 1 mm and 10 cm.

10. The shunt according to claim 1, wherein a maximum length and a maximum width of the shunt is approximately 4 cm, and a minimum length and a minimum width of the shunt is approximately 1 mm.

11. The shunt according to claim 1, wherein a thickness of the shunt is approximately between 1 mm and 1 cm.

12. A method of treating glaucoma using a glaucoma shunt including a catheter, comprising:
    surgically inserting one end of the catheter of the glaucoma shunt into an anterior chamber of an eye; and
    surgically implanting a base plate connected to the catheter beneath a conjunctiva of the eye, the base plate including first and second porous regions connected to each other, and a third region having edge areas attached to edge areas of the second region so as to form a hollow reservoir therebetween,
    wherein at least one of the first, second and third regions comprises a material selected from the group consisting of denucleated polytetrafluoroethylene (ePTFE), denucleated polyurethane, and denucleated elastomeric silicone, in which at least 60% of air trapped within the material is removed, and
    wherein the second region comprises denucleated expanded polytetrafluoroethylene (ePTFE) having pores with diameters less than or equal to 0.8 μm.

13. The method according to claim 12, further comprising:
    suturing the base plate to the sclera of the eye.

14. A glaucoma shunt, comprising:
    a first porous region;
    a second porous region connected to the first porous region and having edge areas;
    a third region having edge areas attached to the edge areas of the second region so as to form a hollow reservoir therebetween; and
    a catheter having an end between the second and third regions,
    wherein the second region comprises expanded polytetrafluoroethylene (ePTFE) having pores with diameters less than or equal to 0.8 μm.

15. A glaucoma shunt, comprising:
    a first porous region;
    a second porous region connected to the first porous region and having edge areas;
    a third region having edge areas attached to the edge areas of the second region so as to form a hollow reservoir therebetween; and
    a catheter having an end between the second and third regions,
    wherein the connected first and second regions have a permeability defined as a water flow through rate of at least 1.0 microliter/min·cm$^2$ at a water entry pressure of 100 mmHg.

16. A glaucoma shunt, comprising:
    a first porous region;
    a second porous region connected to the first porous region and having edge areas;
    a third region having edge areas attached to the edge areas of the second region so as to form a hollow reservoir therebetween; and
    a catheter having an end between the second and third regions,
    wherein the first region comprises denucleated polyurethane having pores with diameters within a range of 1 μm to 500 μm.

17. A glaucoma shunt, comprising:
    a first porous region;
    a second porous region connected to the first porous region and having edge areas;
    a third region having edge areas attached to the edge areas of the second region so as to form a hollow reservoir therebetween; and
    a catheter having an end between the second and third regions, wherein the second region comprises polyurethane having pores with diameters less than or equal to 0.8 µm.

18. A glaucoma shunt, comprising:

a first porous region;

a second porous region connected to the first porous region and having edge areas;

a third region having edge areas attached to the edge areas of the second region so as to form a hollow reservoir therebetween; and a catheter having an end between the second and third regions, wherein the first region comprises denucleated elastomeric silicone having pores with diameters within a range of 1 µm to 500 µm.

19. A glaucoma shunt, comprising:

a first porous region;

a second porous region connected to the first porous region and having edge areas;

a third region having edge areas attached to the edge areas of the second region so as to form a hollow reservoir therebetween; and a catheter having an end between the second and third regions, wherein the second region comprises elastomeric silicone having pores with diameters less than or equal to 0.8 µm.

20. A glaucoma shunt, comprising:

a first porous region;

a second porous region connected to the first porous region and having edge areas;

a third region having edge areas attached to the edge areas of the second region so as to form a hollow reservoir therebetween; and a catheter having an end between the second and third regions, wherein the catheter comprises material selected from the group consisting of silicone, ePTFE, polycarbonate, polyethylene, and polyurethane, and has a length between 1 mm and 10 cm, and wherein the first region includes pores with diameters within a range of 1 µm to 500 µm, and the second region includes pores with diameters less than or equal to 0.8 µm such that blood vessels including arterioles, capillaries and venules penetrate through the pores of the first region but not through the pores of the second region.

21. A glaucoma shunt, comprising:

a first porous region;

a second porous region connected to the first porous region and having edge areas;

a third region having edge areas attached to the edge areas of the second region so as to form a hollow reservoir therebetween; and a catheter having an end between the second and third regions, wherein a maximum length and a maximum width of the shunt is approximately 4 cm, and a minimum length and a minimum width of the shunt is approximately 1 mm, and wherein the first region includes pores with diameters within a range of 1 µm to 500 µm, and the second region includes pores with diameters less than or equal to 0.8 µm such that blood vessels including arterioles, capillaries and venules penetrate through the pores of the first region but not through the pores of the second region.

22. A glaucoma shunt, comprising:

a first porous region;

a second porous region connected to the first porous region and having edge areas;

a third region having edge areas attached to the edge areas of the second region so as to form a hollow reservoir therebetween; and a catheter having an end between the second and third regions, wherein a thickness of the shunt is approximately between 1 mm and 1 cm, and wherein the first region includes pores with diameters within a range of 1 µm to 500 µm, and the second region includes pores with diameters less than or equal to 0.8 µm such that blood vessels including arterioles, capillaries and venules penetrate through the pores of the first region but not through the pores of the second region.

23. A glaucoma shunt, comprising:

a first porous region;

a second porous region connected to the first porous region and having edge areas;

a third region having edge areas attached to the edge areas of the second region so as to form a hollow reservoir therebetween; and a catheter having an end between the second and third regions, wherein the first, second and third porous regions and the catheter form the glaucoma shunt, wherein at least one of the first, second and third regions comprises a material selected from the group consisting of denucleated polytetrafluoroethylene (ePTFE), denucleated polyurethane, and denucleated elastomeric silicone, in which at least 60% of air trapped within the material is removed, and wherein the connected first and second regions have a permeability defined as a water flow through rate of at least 1.0 microliter/min·cm$^2$ at a water entry pressure of 100 mmHg.

24. A glaucoma shunt, comprising:

a first porous region;

a second porous region connected to the first porous region and having edge areas;

a third region having edge areas attached to the edge areas of the second region so as to form a hollow reservoir therebetween; and a catheter having an end between the second and third regions, wherein the first, second and third porous regions and the catheter form the glaucoma shunt, wherein at least one of the first, second and third regions comprises a material selected from the group consisting of denucleated polytetrafluoroethylene (ePTFE), denucleated polyurethane, and denucleated elastomeric silicone, in which at least 60% of air trapped within the material is removed, and wherein the second region comprises denucleated polyurethane having pores with diameters less than or equal to 0.8 µm.

25. A glaucoma shunt, comprising:

a first porous region;

a second porous region connected to the first porous region and having edge areas;

a third region having edge areas attached to the edge areas of the second region so as to form a hollow reservoir therebetween; and a catheter having an end between the second and third regions, wherein the first, second and third porous regions and the catheter form the glaucoma shunt, wherein at least one of the first, second and third regions comprises a material selected from the group consisting of denucleated polytetrafluoroethylene (ePTFE), denucleated polyurethane, and denucleated elastomeric silicone, in which at least 60% of air trapped within the material is removed, and wherein the first region comprises denucleated elastomeric silicone having pores with diameters within a range of 1 $\mu$m to 500 $\mu$m.

26. A glaucoma shunt, comprising:

a first porous region;

a second porous region connected to the first porous region and having edge areas;

a third region having edge areas attached to the edge areas of the second region so as to form a hollow reservoir therebetween; and a catheter having an end between the second and third regions, wherein the first, second and third porous regions and the catheter form the glaucoma shunt, wherein at least one of the first, second and third regions comprises a material selected from the group consisting of denucleated polytetrafluoroethylene (ePTFE), denucleated polyurethane, and denucleated elastomeric silicone, in which at least 60% of air trapped within the material is removed, and wherein the second region comprises denucleated elastomeric silicone having pores with diameters less than or equal to 0.8 $\mu$m.

27. A method of treating glaucoma using a glaucoma shunt including a catheter, comprising:

surgically inserting one end of the catheter of the glaucoma shunt into an anterior chamber of an eye; and surgically implanting a base plate connected to the catheter beneath a conjunctiva of the eye, the base plate including first and second porous regions connected to each other, and a third region having edge areas attached to edge areas of the second region so as to form a hollow reservoir therebetween, wherein at least one of the first, second and third regions comprises a material selected from the group consisting of denucleated polytetrafluoroethylene (ePTFE), denucleated polyurethane, and denucleated elastomeric silicone, in which at least 60% of air trapped within the material is removed, and wherein the connected first and second regions have a permeability defined as a water flow through rate of at least 1.0 microliter/min·cm$^2$ at a water entry pressure of 100 mmHg.

28. A method of treating glaucoma using a glaucoma shunt including a catheter, comprising:

surgically inserting one end of the catheter of the glaucoma shunt into an anterior chamber of an eye; and surgically implanting a base plate connected to the catheter beneath a conjunctiva of the eye, the base plate including first and second porous regions connected to each other, and a third region having edge areas attached to edge areas of the second region so as to form a hollow reservoir therebetween, wherein at least one of the first, second and third regions comprises a material selected from the group consisting of denucleated polytetrafluoroethylene (ePTFE), denucleated polyurethane, and denucleated elastomeric silicone, in which at least 60% of air trapped within the material is removed, and wherein the second region comprises denucleated polyurethane having pores with diameters less than or equal to 0.8 $\mu$m.

29. A method of treating glaucoma using a glaucoma shunt including a catheter, comprising:

surgically inserting one end of the catheter of the glaucoma shunt into an anterior chamber of an eye; and surgically implanting a base plate connected to the catheter beneath a conjunctiva of the eye, the base plate including first and second porous regions connected to each other, and a third region having edge areas attached to edge areas of the second region so as to form a hollow reservoir therebetween, wherein at least one of the first, second and third regions comprises a material selected from the group consisting of denucleated polytetrafluoroethylene (ePTFE), denucleated polyurethane, and denucleated elastomeric silicone, in which at least 60% of air trapped within the material is removed, and wherein the first region comprises denucleated elastomeric silicone having pores with diameters within a range of 1 $\mu$m to 500 $\mu$m.

30. A method of treating glaucoma using a glaucoma shunt including a catheter, comprising:

surgically inserting one end of the catheter of the glaucoma shunt into an anterior chamber of an eye; and surgically implanting a base plate connected to the catheter beneath a conjunctiva of the eye, the base plate including first and second porous regions connected to each other, and a third region having edge areas attached to edge areas of the second region so as to form a hollow reservoir therebetween, wherein at least one of the first, second and third regions comprises a material selected from the group consisting of denucleated polytetrafluoroethylene (ePTFE), denucleated polyurethane, and denucleated elastomeric silicone, in which at least 60% of air trapped within the material is removed, and wherein the second region comprises denucleated elastomeric silicone having pores with diameters less than or equal to 0.8 $\mu$m.

* * * * *

UNITED STATES PATENT AND TRADEMARK OFFICE
CERTIFICATE OF CORRECTION

PATENT NO. : 6,699,210 B2
DATED : March 2, 2004
INVENTOR(S) : Williams et al.

It is certified that error appears in the above-identified patent and that said Letters Patent is hereby corrected as shown below:

<u>Title page</u>,
Item [73], Assignee, should read

-- [73] Assignee: The Arizona Board of Regents acting on behalf of The University of Arizona, Tucson, AZ (US) --

Signed and Sealed this

Twenty-seventh Day of April, 2004

JON W. DUDAS
*Acting Director of the United States Patent and Trademark Office*